(12) United States Patent
Taniguchi

(10) Patent No.: US 9,737,281 B2
(45) Date of Patent: Aug. 22, 2017

(54) ULTRASOUND DIAGNOSTIC EQUIPMENT

(75) Inventor: Tetsuya Taniguchi, Hachioji (JP)

(73) Assignee: KONICA MINOLTA MEDICAL & GRAPHIC, INC., Tokyo (JP)

( * ) Notice: Subject to any disclaimer, the term of this patent is extended or adjusted under 35 U.S.C. 154(b) by 110 days.

(21) Appl. No.: 13/634,771

(22) PCT Filed: Feb. 24, 2011

(86) PCT No.: PCT/JP2011/054100
§ 371 (c)(1),
(2), (4) Date: Sep. 13, 2012

(87) PCT Pub. No.: WO2011/114852
PCT Pub. Date: Sep. 22, 2011

(65) Prior Publication Data
US 2013/0006113 A1    Jan. 3, 2013

(30) Foreign Application Priority Data

Mar. 16, 2010   (JP) ................. 2010-059021

(51) Int. Cl.
*A61B 8/00*   (2006.01)
*A61B 8/08*   (2006.01)
(Continued)

(52) U.S. Cl.
CPC .............. *A61B 8/08* (2013.01); *A61B 8/5207* (2013.01); *A61B 8/5269* (2013.01);
(Continued)

(58) Field of Classification Search
CPC .................... G01S 15/8952; G01S 7/52047
(Continued)

(56) References Cited

U.S. PATENT DOCUMENTS 4,646,748 A * 3/1987 Fujii et al. ................. 600/441
4,689,986 A * 9/1987 Carson ................. A61B 8/481
                                                     600/438

(Continued)

FOREIGN PATENT DOCUMENTS

JP       5-168630 A    7/1993
JP    2001-238884 A    9/2001
(Continued)

OTHER PUBLICATIONS

International Search Report dated May 24, 2011 issued in International Appln. No. PCT/JP2011/054100.
(Continued)

*Primary Examiner* — Jonathan Cwern
(74) *Attorney, Agent, or Firm* — Holtz, Holtz & Volek PC

(57) ABSTRACT

An ultrasound diagnostic equipment is equipped with an ultrasound probe which transmits an ultrasound wave toward an inner part of a subject and receives the ultrasound wave reflected with a particle body in the subject and acquires a received signal to displays internal body information in the subject based on the received signal. The ultrasound diagnostic equipment includes: an acquisition section to acquire the received signal for each of ultrasound waves of which frequencies differ; an intensity ratio calculation section to calculate an intensity ratio of the ultrasound wave for each of frequencies; and a display section to display the information on the intensity ratio.

8 Claims, 7 Drawing Sheets

(51) Int. Cl.
*G01S 7/52* (2006.01)
*G01S 15/89* (2006.01)

(52) U.S. Cl.
CPC ...... *G01S 7/52036* (2013.01); *G01S 15/8952* (2013.01); *A61B 8/4472* (2013.01); *G01S 7/52047* (2013.01)

(58) Field of Classification Search
USPC ......................................................... 600/443
See application file for complete search history.

(56) References Cited

U.S. PATENT DOCUMENTS

| | | | |
|---|---|---|---|
| 5,749,364 A * | 5/1998 | Sliwa et al. ................. | 600/438 |
| 6,408,679 B1 * | 6/2002 | Kline-Schoder ......... | A61B 8/08 73/19.03 |
| 2003/0060707 A1 | 3/2003 | Ogawa | |
| 2005/0203405 A1 | 9/2005 | Tsujita | |
| 2008/0319317 A1 | 12/2008 | Kamiyama et al. | |
| 2009/0062655 A1 * | 3/2009 | Saito ............................ | 600/459 |
| 2009/0130561 A1 * | 5/2009 | Matsumoto et al. ...... | 429/231.8 |

FOREIGN PATENT DOCUMENTS

| | | |
|---|---|---|
| JP | 2003-093383 A | 4/2003 |
| JP | 2005-253827 A | 9/2005 |
| JP | 2007-268155 A | 10/2007 |

OTHER PUBLICATIONS

Japanese Office Action dated Nov. 4, 2014, issued in counterpart Japanese Application No. 2012-505585.

* cited by examiner

ULTRASOUND DIAGNOSTIC EQUIPMENT

This application is a U.S. National Phase Application under 35 USC 371 of International Application PCT/JP2011/054100 filed Feb. 24, 2011.

TECHNICAL FIELD OF THE INVENTION

The present invention relates to an ultrasound diagnostic equipment which transmits an ultrasound signal toward an inner part of a subject and generates an ultrasound image of the inner part of the subject based on a reflective wave.

PRIOR ART

An ultrasound wave usually represents a sound wave of 16000 Hz or more, and is applied to various fields such as a defect inspection and a diagnosis of diseases, because the inner parts can be checked non-destructively, harmlessly and in approximately real time. As one of such applications, an ultrasound diagnostic equipment carries out an ultrasound imaging of an internal state of a subject based on the received signal generated from the reflective wave of the ultrasound wave from the inner part of the subject by allowing an ultrasound probe scan the inner part of the subject. The ultrasound diagnostic equipment is relatively low in cost and small compared with other imaging equipments for medical use, and is high in safety because no radiation of X-rays and so on is irradiated. Further, it has various features such that it is possible to obtain medical images such as B mode images by performing an envelope curve detection processing to the reflective wave of the ultrasound wave. For this reason, the ultrasound diagnostic equipment is widely used by circulatory organ systems (for example, coronary arteries of the heart and so on.), digestive systems (for example, stomach and intestines and so on.), the internal medicine system (for example, liver, pancreas, spleen, and so on.), urinary-organs systems (for example, the kidney, a bladder, and so on.), an obstetrics-and-gynecology system, and so on.

On an ultrasound image, the speckle pattern resulting from a random interference of the ultrasound wave may be generated. Although the speckle pattern is used for diagnosis of liver cirrhosis and so on, in the case of mammography screening, there is a close resemblance between the speckle pattern and a minute structure such as a microcalcification, and the speckle pattern will be a confusing image information in the mammography screening. There is a request of wanting to improve the accuracy of a medical checkup by extracting and removing the speckle pattern in mammography screening and so on.

As a technology for encountering this, there is technology for removing a speckle pattern from the ultrasound image information, distinguishing a minute structure such as a microcalcification from a continuation structure, by a two-dimensional or three-dimensional continuity and extracting the minute structure (for example, refer to patent document 1).

Further, there is a technology of acquiring an echo level probability-density-distribution information on the speckle pattern obtained as a result of the mutual interference of a Rayleigh dispersion, and acquiring organization behavior information by a gap from the Rayleigh distribution of the distribution curve (for example, refer to patent document 2).

PRIOR TECHNICAL DOCUMENTS

Patent Documents

[Patent document 1] Japanese Unexamined Patent Application Publication 2007-268155
[Patent document 2] Japanese Unexamined Patent Application Publication 2001-238884

SUMMARY OF THE INVENTION

Problems to be Solved by the Present Invention

The technology described in the patent document 1 is a method for extracting a minute structure from ultrasound image information in image processing, and the extraction processing is performed only from the image-informatized information, the information in respect to the size about the minute scattered object smaller than a sound ray pitch is not acquired. Further, when microcalcifications exist continuous within a mammary duct, it is difficult to distinguish the calcifications from continuation structures, such as organizational boundaries, and it may be unable to extract the calcifications.

In the technology described in the patent documents 2, a state of a certain whole region is judged by processing statistically image information such as a speckle pattern obtained from the result of the mutual interference of Rayleigh dispersion, and it is difficult to extract extraction structures such as a microcalcification.

An object of the present invention is to supply the ultrasound diagnostic equipment which is capable of extracting even microcalcifications which exist continuously by transmitting sound waves having a wide band frequency and calculating of particle radii of particle bodies by the difference in frequency component ratios in the reflective ultrasound wave, and is capable of acquiring the particle radii of the particle bodies simultaneously.

Means to Solve the Problems

The above-mentioned object can be achieved by inventions described below.
1. An ultrasound diagnostic equipment which is equipped with an ultrasound probe which transmits an ultrasound wave toward an inner part of a subject and receives the ultrasound wave reflected by a particle body in the subject and acquires a received signal to display an internal body information in the subject based on the received signal, the ultrasound diagnostic equipment comprising:
an acquisition section to acquire the received signal for each of ultrasound waves of which frequencies differ;
an intensity ratio calculation section to calculate an intensity ratio by acquiring an intensity of the ultrasound wave for each of frequencies from the acquired received signal for each of the ultrasound waves; and
a display section to display an information on the intensity ratio.
2. The ultrasound diagnostic equipment described in the item 1, comprising a particle radius calculation section to calculate a particle radius of the particle body based on the information on the intensity ratio which the intensity ratio calculation section calculated, in place of the display section.

3. The ultrasound diagnostic equipment described in the item 2, comprising a display section to display the particle radius calculated by the particle radius calculation section.

4. The ultrasound diagnostic equipment described in the item 2, comprising a section which extracts the particle body which has the particle radius of a range specified automatically or arbitrarily based on a calculation result of the particle radius calculation section and carries out imaging of the particle body.

5. The ultrasound diagnostic equipment described in any one of items 1 thorough 4, wherein the ultrasound probe has a −20 dB fractional bandwidth which is not less than 80%.

6. The ultrasound diagnostic equipment described in any one of items 1 thorough 5, wherein the ultrasound probe includes a piezo-electric element which transmits a ultrasound wave and a transmitting section which drives the piezo-electric element, wherein the transmitting section drives the piezo-electric element by a burst wave of a rectangular wave of a duty cycle not more than of 0.3.

7. The ultrasound diagnostic equipment described in any one of items 1 thorough 5, wherein the ultrasound probe transmits the ultrasound wave of a plane wave.

Effects of the Invention

The ultrasound diagnostic equipment which is capable of extracting even the microcalcifications which exist continuously and, at the same time, is capable of grasping the particle radii of particle bodies is provided.

BRIEF DESCRIPTION OF THE DRAWINGS

FIG. 8 is a figure showing a relation of Z function of Stenzel and k·a.

DETAILED DESCRIPTION OF THE INVENTION

Although the embodiment of the invention is explained below with drawings, the present invention is not restricted to the embodiment explained below. Further, the composition to which the same mark is attached in each figure represents the same composition, and the explanation is omitted.

Figure 1:
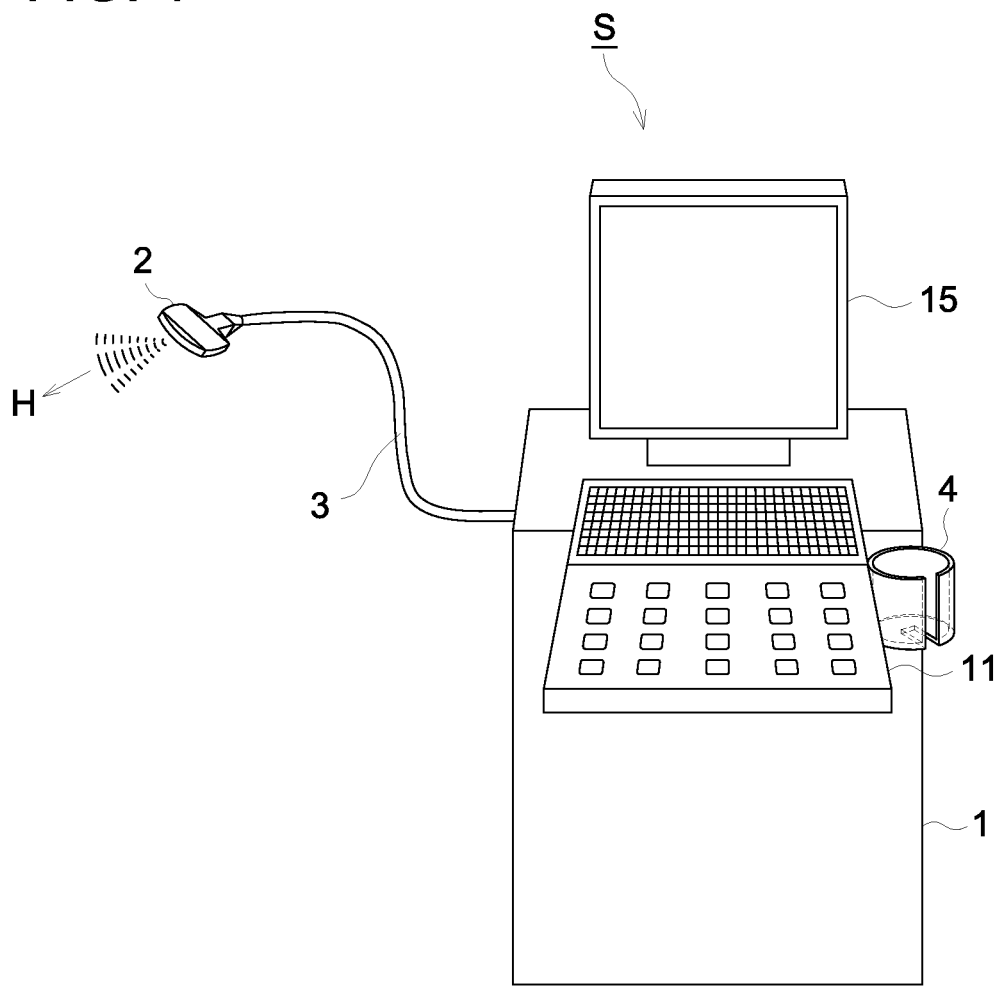
FIG. 1 is a schematic drawing showing an appearance composition of the ultrasound diagnostic equipment relating to an embodiment.
Figure 2:
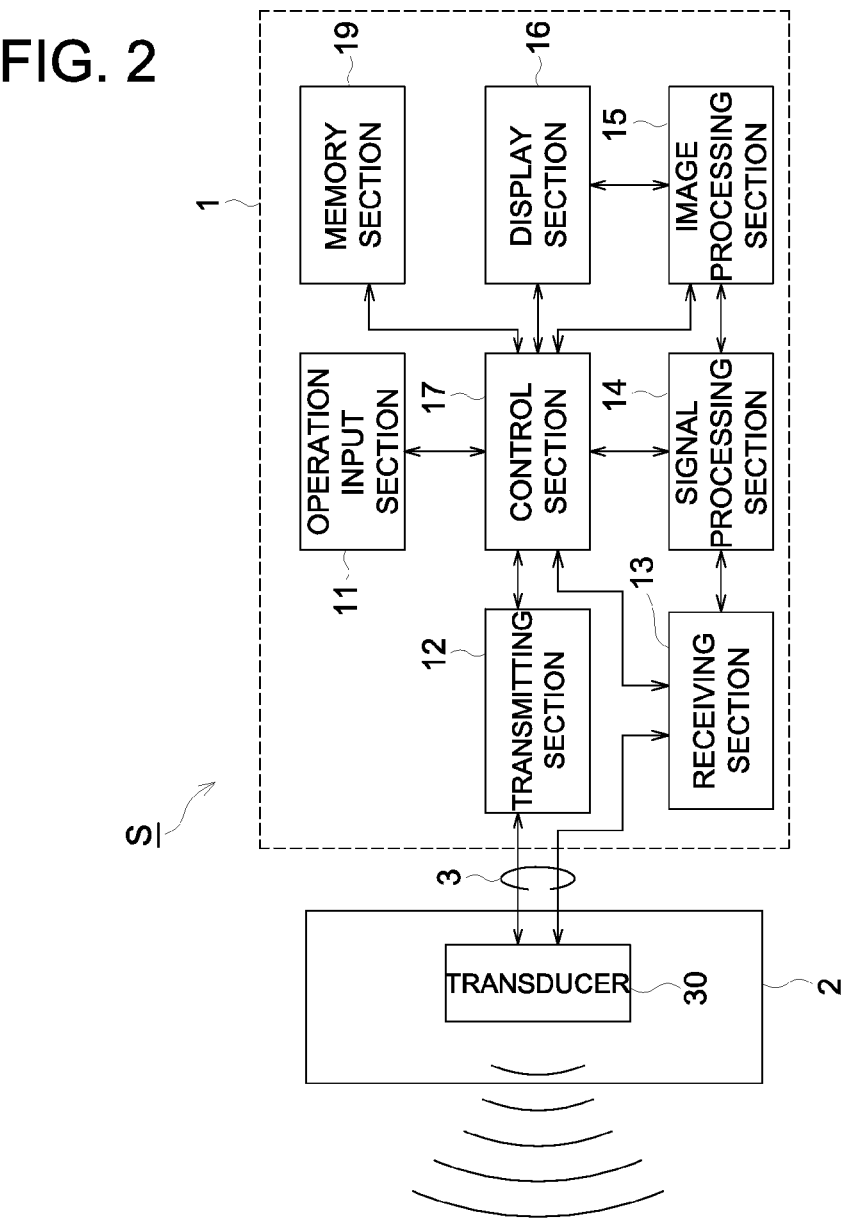
FIG. 2 is a block diagram showing an electric composition of the ultrasound diagnostic equipment relating to the embodiment.
Figure 3:
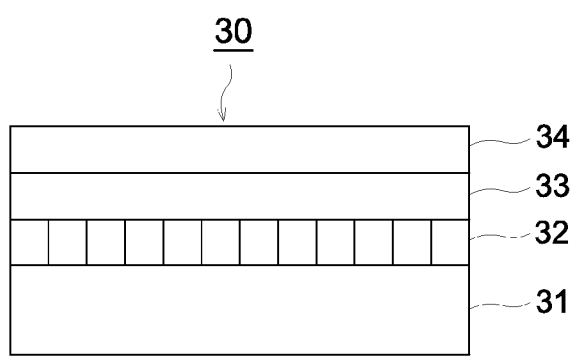
FIG. 3 is a schematic drawing showing the composition of the ultrasound probe of the ultrasound diagnostic equipment relating to the embodiment.

FIG. 1 is a schematic drawing showing the appearance composition of the ultrasound diagnostic equipment relating to the embodiment. FIG. 2 is a block diagram showing the electric composition of the ultrasound diagnostic equipment relating to an embodiment. FIG. 3 is a schematic drawing showing the composition of the ultrasound probe of the ultrasound diagnostic equipment relating to an embodiment.

As shown in FIGS. 1 and 2, the ultrasound diagnostic equipment S is configured by comprising an ultrasound probe 2 which transmits an ultrasound signal (it is also henceforth called a first ultrasound wave signal) to the subject H such as a living body (not shown), and receives a reflective wave (it is also henceforth called a second ultrasound wave signal) of the ultrasound signal reflected by subject H, and an ultrasound diagnostic equipment main body 1 which connects with the ultrasound probe 2 through a cable 3, makes the ultrasound probe 2 transmit the first ultrasound wave signal to the subject H by transmitting the transmitting signal of an electric signal to the ultrasound probe 2 through a cable 3, and carries out imaging to a medical image by making the internal state in the subject H into an ultrasound image based on the received signal of the electric signal generated by the ultrasound probe 2 according to the second ultrasound wave signal received by the ultrasound probe 2 from the subject H. The ultrasound diagnostic equipment main body 1 is equipped with an ultrasound probe holder 4 which holds the ultrasound probe 2 when the ultrasound probe 2 is not used.

As shown in FIG. 2, for example, the ultrasound diagnostic equipment main body 1 is constituted by comprising an operation input section 11, a transmitting section 12 and receiving section 13 of the present invention, a signal processing section 14 of the present invention, an image processing section 15, a display section 16, a control section 17, and a memory section 19.

The operation input section 11 through which, for example, a command to direct a diagnostic start and data such as a personal information on the subject H are inputted, is an operation panel equipped with plural switches or a keyboard and so, for example.

The transmitting section 12 of the present invention supplies the transmitting signal through the cable 3 to the piezo-electric section 32 in the ultrasound probe 2, and makes the ultrasound probe 2 generate the first ultrasound wave signal. The transmitting section 12 is constituted by equipping with a high voltage pulse generator which generates a high voltage pulse, for example, and makes the ultrasound probe 2 transmit the first ultrasound wave signal which has harmonics frequency components other than a fundamental frequency component to the subject H. The details are explained later.

Further, the piezo-electric section 32 may consist of two piezo-electric sections which are a piezo-electric section for transmission and a piezo-electric section for reception.

The receiving section 13 is a circuit which receives the received signal of an electric signal through the cable 3 from the ultrasound probe 2 according to the control of the control section 17, and outputs this received signal to the signal processing section 14. The receiving section 13 is constituted by equipping with the amplifier which amplifies a received signal at the predetermined amplification rate which has been set up beforehand, for example, an analogto-digital converter which converts the received signal amplified by the amplifier from an analog signal into a digital signal, and so on.

The signal processing section 14 of the present invention is a circuit which performs a predetermined signal processing to the electric signal from the receiving section 13, according to the control of the control section 17, and outputs the reflective received signal subject to a predetermined signal processing, to the image processing section 15. The reflective signal includes a reflective signal based on the fundamental frequency component and the harmonic frequency component which the transmitting section 12 generated, and the signal processing section 14 performs a signal processing for each frequency component. The details are explained later.

The image processing section 15 is a circuit which generates the ultrasound image of the internal state in the subject H using a harmonic imaging technology and so on based on the reflective received signal to which the signal processing was performed in the signal processing section 14 according to the control of the control section 17. For example, B mode signal corresponding to an amplitude intensity of the second ultrasound wave signal is generated by performing an envelope curve detection processing to the reflective received signal.

The memory section 19 is constituted by comprising RAM or ROM. A program used for the control section 17 and a template of the various images to be displayed in the display section 16 are recorded in the memory section 19.

The display section 16 is an equipment which displays a synthetic image synthesized in the image synthesizing section 18 according to the control of the control section 17 as an internal body information. The display section 16 is a display device such a CRT display, an LCD, an EL display, a plasma display, and so on, or a printing device such as a printer, for example.

The control section 17 is a circuit which is configured by equipping, for example, a microprocessor, a storage device, a peripheral circuit thereof, and so on, and performs a whole control of the ultrasound diagnostic equipment S by controlling the operation input section 11 for them, the transmitting section 12, the receiving section 13, the signal processing section 14, the image processing section 15, the image synthesizing section 18, and the memory section 19 corresponding to each of the functions.

On the other hand, the ultrasound probe 2 is equipped with the transducer 30. The transducer 30 transmits the first ultrasound wave signal to the subject H, such as a living body (not shown in the drawing), and receives the second ultrasound wave signal from the subject H. The transducer 30 is constituted by having, for example, an acoustic inhibiting member 31, a piezo-electric section 32, a sound adjustment layer 33, and an acoustic lens 34 as shown in FIG. 3.

The acoustic inhibiting member 31 is a plate shaped member consisted of material absorbing an ultrasound wave, and absorbs the ultrasound wave emitted toward the acoustic inhibiting member 31 from the piezo-electric section 32.

The piezo-electric section 32 is constituted by having a piezo-electric material and transduces a signal mutually between an electric signal and an ultrasound signal by using a piezo-electric phenomenon. The piezo-electric section 32 transduces the electric signal of the transmitting signal inputted through the cable 3 from the transmitting section 12 of the ultrasound diagnostic equipment main body 1 into the first ultrasound wave signal to transmit the first ultrasound wave signal, and outputs the received signal which is an electric signal to which the received second ultrasound wave signal is transduced, to the receiving section 13 of the ultrasound diagnostic equipment main body 1 through the cable 3. When the ultrasound probe 2 is contacted to the subject H, the first ultrasound wave signal generated in the piezo-electric section 32 is transmitted into the subject H, and the second ultrasound wave signal from the subject H is received by the piezo-electric section 32.

The piezo-electric section 32, for example, in the present embodiment, is constituted by having a piezo-electric material and can employ a common piezo-electric materials such as lead zirconate titanate which can change a signal mutually between an electric signal and an ultrasound signal by using a piezo-electric phenomenon. Other than this, an organic piezo-electric material such as a polymer of vinylidene fluoride, and the copolymer of vinylidene fluoride and trifluoroethylene, for example, can be used. Since the electromechanical coupling coefficient (piezo-electric effect) in the thickness direction changes with copolymerization ratios in the case of the copolymer of vinylidene fluoride and trifluoroethylene, for example, the copolymerization ratio of 60-99 mol % is desirable. Further, such organic piezo-electric materials are suitable as a piezo-electric material which has the high frequency characteristic and the broadband characteristic.

With this embodiment, the electric signal is inputted through the cable 3 from the transmitting section 12 of the ultrasound diagnostic equipment main body 1, and the piezo-electric section 32 transduces the electric signal into the first ultrasound wave signal, and transmits the transduced first ultrasound wave signal to the subject H through the sound adjustment layer 33 and the acoustic lens 34. And the piezo-electric section 32 receives the second ultrasound wave signal from the subject H through the acoustic lens 34 and the sound adjustment layer 33, transduces the received second ultrasound wave signal into an electric signal, and outputs the transduced electric signal to the receiving section 13 of the ultrasound diagnostic equipment main body 1 through the cable 3 as a received signal.

Subsequently, the transmitting section 12, the signal processing section 14, and so on of the present invention are explained in detail.

Figure 4:
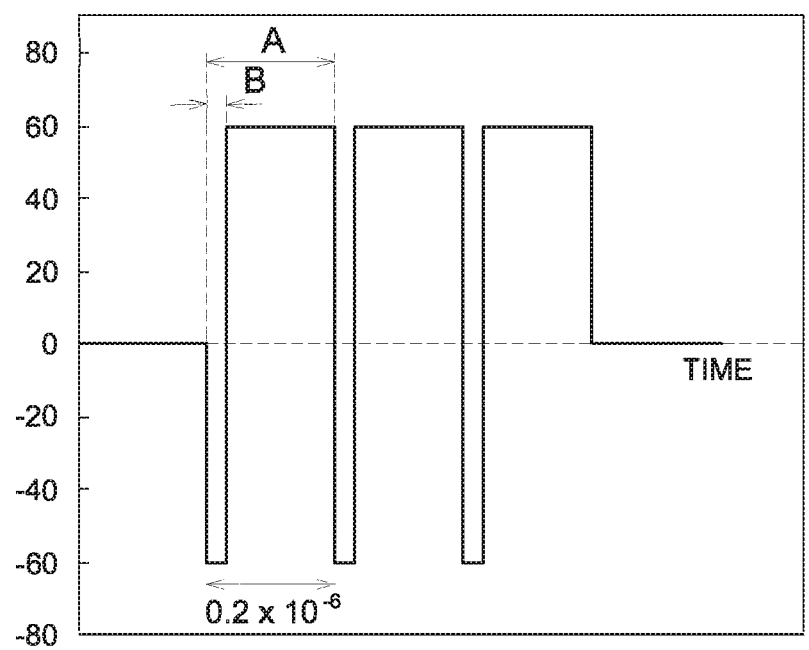
FIG. 4 is an example of a voltage waveform of the drive electric signal.

The transmitting section 12 generates the drive electric signal which has not only a single frequency component but also plural frequency components of a large frequency difference as the transmitted wave used for extracting particles. FIG. 4 shows an example of a voltage waveform of the drive electric signal. The horizontal axis expresses time and the vertical axis expresses the drive voltage.

The drive voltage waveform relating to the embodiment is a rectangle wave burst wave, and is a wave form of a duty cycle of 0.3 or less. A duty cycle is a ratio (B/A) of the time of a shorter rectangle which constitutes 1 cycle of the rectangle wave to the time of 1 cycle. The rectangle wave has high order frequency components by a Fourier series expansion, and the amplitude of the high order frequency can be enlarged by making the duty cycle in a rectangle wave small. That is, the rectangle wave has of a duty cycle of 0.3 or less has a wider amplitude compared with such a rectangle wave of the duty cycle of 0.5. Further, the rectangle wave shown in FIG. 4 has a fundamental period of 5 MHz.

The transmitting section 12 is equipped with a high voltage pulse generator which has a known pulse generator function (not shown in drawings) which can generate this rectangle wave.

Figure 5:
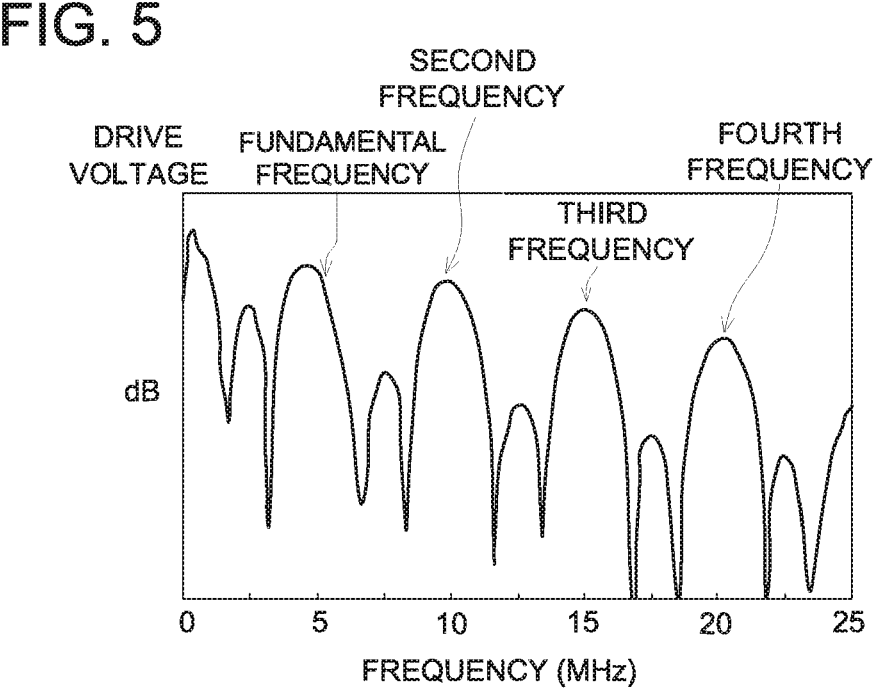
FIG. 5 shows the calculation result of a spectrum in the drive electric signal of FIG. 4 which the transmitting section 12 generated.

FIG. 5 shows the calculation result of the spectrum in the drive electric signal of FIG. 4 which the transmitting section 12 generated. A horizontal axis expresses frequency and a vertical axis expresses the drive voltage displaying relatively with dB.

The drawing shows that, other than 5 MHz component, frequency components which correspond 2 to 4 times of the frequency are included. Further, since the drive electric signal is a burst wave, the drive electric signal has a short frequency component below the fundamental frequency based on an envelope curve, and the satellite frequency component has occurred between the harmonic waves based on the short frequency component and the harmonics components.

Figure 6:
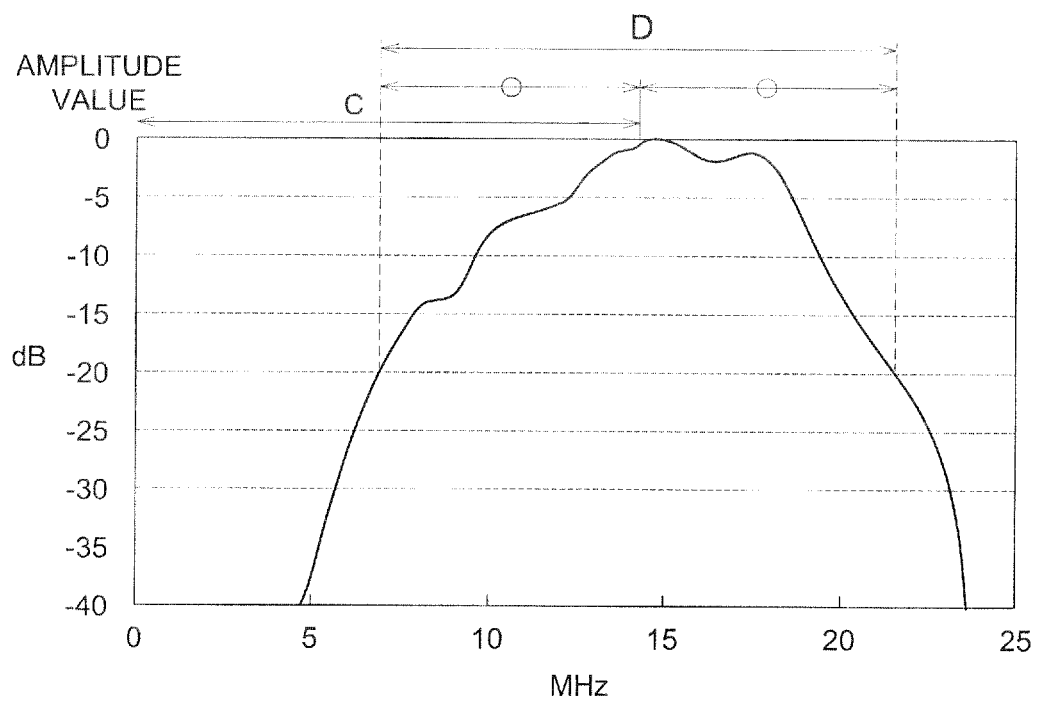
FIG. 6 is a typical diagram showing an example of a band width characteristic in the transmission and reception of the ultrasound probe 2.

Further, the ultrasound probe 2 has the frequency characteristic of the ultrasound probe itself. FIG. 6 is a typical diagram showing an example of the band characteristic in transmission and reception of the ultrasound probe 2. That is, the frequency characteristic of the amplitude value of the sound pressure of the first ultrasound wave signal to transmit is expressed. In the drawing, the bandwidth of which an amplitude value falls by −20 dB is set to D, the center value of the band set to C, and −20 dB ratio bandwidth is defined as D/C.

Figure 7:
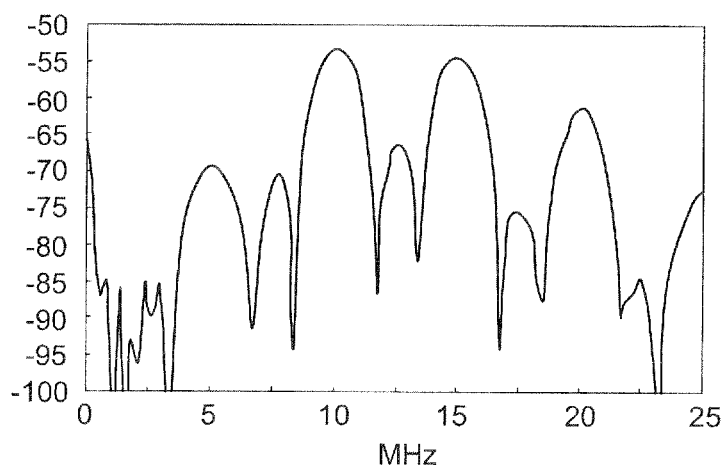
FIG. 7 is a figure showing a frequency spectrum of a sound pressure of the first ultrasound wave signal when the transmitting signal shown in FIG. 4 is inputted to the ultrasound probe 2.

FIG. 7 expresses the frequency spectrum of the sound pressure of the first ultrasound wave signal when the transmitting signal shown in FIG. 4 is inputted to the ultrasound probe 2 which has the frequency characteristic like this.

The frequency spectrum of the sound pressure of the first ultrasound wave signal becomes a multiplication of the frequency characteristics of the transmitting signal and the ultrasound probe 2.

Further, the transmitting section 12 performs a transmitting beam forming processing, and has a function which converges the first ultrasound wave signal on the subject.

Next, the signal processing section 14 of the present invention is explained in detail.

In the signal processing section 14, an ultrasound image is individually generated for each frequency. Especially in the embodiment, the calculation of the particle radius of a particle body which is a microcalcification is performed in a mammography screening. In the domain of this particle radius, the dispersion characteristic is in the domain of the characteristic of Rayleigh dispersion.

When a sound pressure P at the position of the ultrasound probe when the particle body (reflecting body of radius a) locates at a distance x from the ultrasound probe which is a sound source and a reflective wave pressure Pr at the position of the ultrasound probe position when the rigid plane surface is located at the position of the particle body are presumed, a reflective power R which is a ratio of these can be expressed with the following formula:

$$R = P/Pr = 2aZ/x \quad (1)$$

Figure 8:
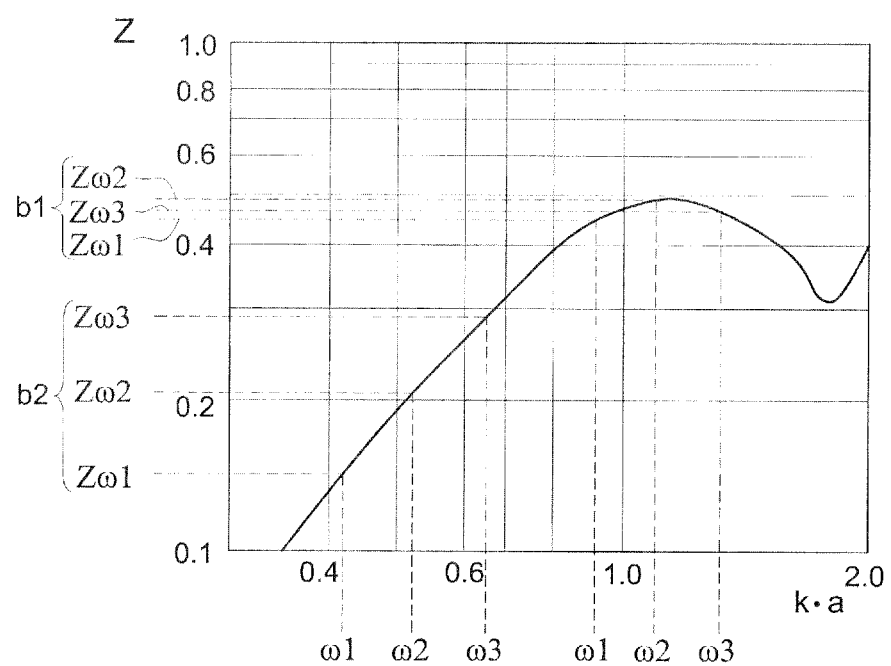

Where, Z is Z function of Stenzel and is shown in FIG. 8. In FIG. 8, k is $\omega/c$, where $\omega$ is the frequency of the ultrasound wave and c is the speed of the ultrasound wave. Please refer to "Ultrasound Technical Handbook" (Nikkan Kogyo Shimbun, the fifth printing of the new edition) for details.

The formula leads a relation that, in the domain of Rayleigh dispersion, the particle radius a and the sound pressure P at the position of the ultrasound probe are approximately proportional. Therefore, for example, the ultrasound signal of plural frequencies is irradiated to the particle body, a frequency analysis of the second ultrasound wave signal reflected from the particle body is conducted, and the reflective power R is measured for each frequency which has been transmitted. By computing the ratio (namely, intensity ratio) of the reflective power for each frequency from the measurement result, the information on the intensity ratio can be displayed on the display section. Furthermore, the particle radius a of the reflecting body can be computed from the ratio of the reflective power for each frequency. That is, the signal processing section 14 has a function as an intensity ratio calculation section to calculate the intensity ratio by acquiring the intensity of the ultrasound wave for each frequency and calculating the intensity ratio from the acquired intensities, and a function as a particle radius calculation section to calculate the particle radius a of the reflecting body.

For example, the first ultrasound wave signals which have three frequencies, $\omega 1$, $\omega 2$, and $\omega 3$, respectively are transmitted to the particle body, and the reflective powers $R\omega 1$, $R\omega 2$, and $R\omega 3$ at the time when each first ultrasound wave signal is reflected with the particle body are measured. And the ratio of reflective power, i.e., the intensity ratio, is displayed on the display section 16. Furthermore, by using the relation between reflective power R and Z function as defined in formula (1), the relation among the Z functions $Z\omega 1$, $Z\omega 2$, and $Z\omega 3$ for each frequency is calculated as depicted in FIG. 8. For example, if the Z functions $Z\omega 1$, $Z\omega 2$, and $Z\omega 3$ have a relation b1 in FIG. 8, it will turn out that $\omega 1$, $\omega 2$, and $\omega 3$ have a positional relationship as shown in the drawing, and the particle radius a equivalent to the relation will become clear. Further, if Z functions $Z\omega 1$, $Z\omega 2$, and $Z\omega 3$ have a relation b2 in FIG. 8, it will turn out that $\omega 1$, $\omega 2$, and $\omega 3$ has a positional relationship as shown in the drawing, and the particle radius a equivalent to the relation will become clear.

Figure 9:
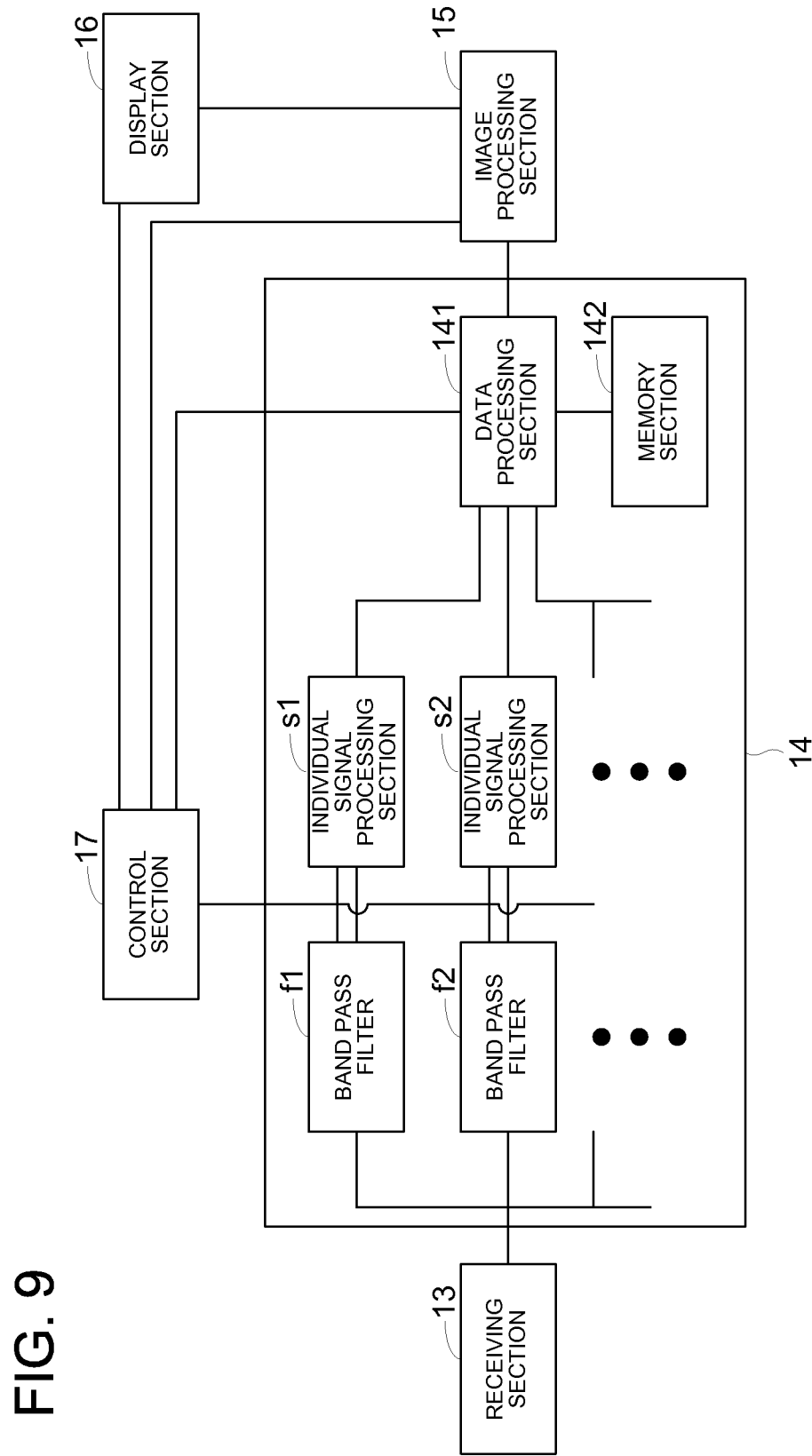
FIG. 9 is an electric block diagram showing the details of the signal processing section 14.
Figure 10A:
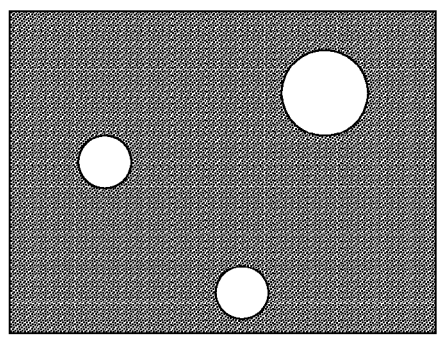
FIG. 10 is a typical diagram showing an example of the ultrasound image for each particle radius.
Figure 10B:
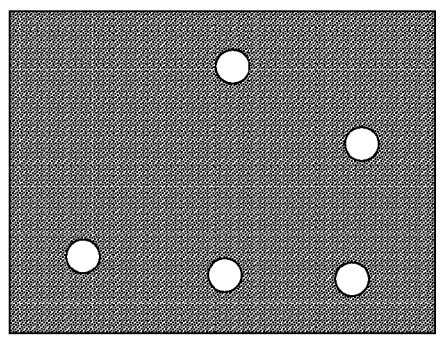
Figure 10C:
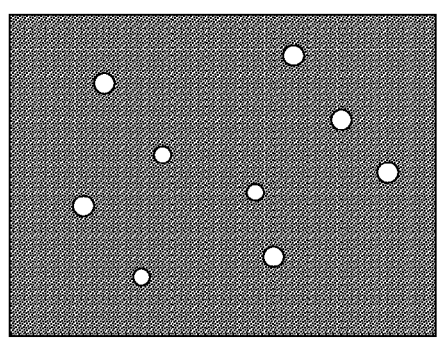
Figure 10D:
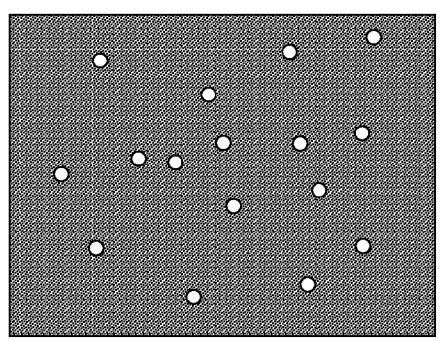
Figure 10E:
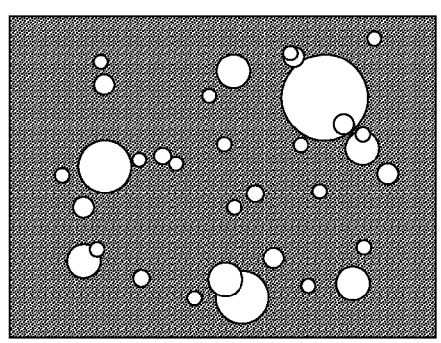
Figure 10F:
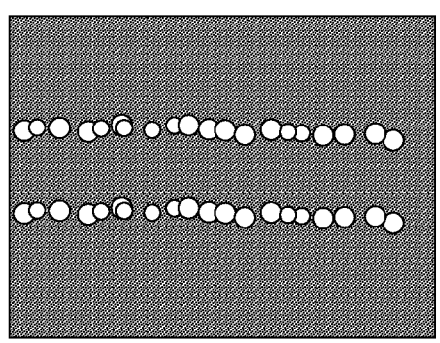

This signal processing is realized by the circuit shown in FIG. 9. FIG. 9 is an electric block diagram showing the details of the signal processing section 14. The signal processing section 14 has band pass filters fn and individual signal processing sections sn (n is a natural number). The received signal from the receiving section 13 is inputted into the band pass filters f1 through fn of n numbers which are provided in the signal processing section 14. The band pass filter is an electric filter which passes only the electric signal of the n-th frequency, and known multiplex feedback filter which is constituted by, for example, an operational amplifier, a resistor, and a capacitor can be used. The electric signal which passed through the band pass filter fn is inputted into the individual signal processing section sn, and is subjected to an AD conversion processing, a receiving apodization processing, a phasing addition processing, an envelope curve detection processing, and so on, and the reflective power R for each frequency is measured.

The reflective power R for each frequency is inputted into the data processing section 141, and the ratio of the reflective power R for each frequency is calculated. In the memory section 142, the relation of the Z function of Stenzel and k·a shown in FIG. 8 is memorized. Specifically, the ratios of the reflective powers $R\omega 1$, $R\omega 2$, and $R\omega 3$ and their relations to the particle radius a are memorized. The data processing section 141 deduces the particle radius a with reference to the memory section 142.

Further, since the ultrasound wave of plural frequencies is transmitted with one ultrasound probe 2 as mentioned above, the relative bandwidth is preferable to be 80% or more so that the ultrasound probe 2 can transmit the ultrasound wave of plural frequencies. When the relative bandwidth is 80% or more, a large number of high order harmonics can be transmitted at once.

In the image processing section 15, the ultrasound image for each particle radius is generated from the electric signal which is processed for each frequency in the signal processing section 14 and the information on the particle radius.

According to the control of the control section 17, the image processing section 15 superimposes all the ultrasound images for each particle radius, or superimposes only ultrasound images of selected frequencies, and data processes the superimposed ultrasound images to input into the display section 16. A user can selects the ultrasound image displayed on the display section 16 in the operation input section 11. The specified range of the particle radii in the ultrasound image for each particle radius can be specified automatically or arbitrarily. Further, the range of a part or all of the ultrasound image can be specified automatically or arbitrarily to perform imaging.

FIG. 10 is a typical diagram showing an example of the ultrasound image for each particle radius. The particle radius becomes smaller as it goes from FIG. 10 (a) to FIG. 10 (d). FIG. 10 (e) shows the image which is obtained by adding all the images from FIG. 10 (a) thorough FIG. 10 (d).

Further, FIG. 10 (f) shows the ultrasound image in which microcalcifications of minute particle shapes exist continuously. If the ultrasound diagnostic equipment S relating to this embodiment is used, the ultrasound image of the minute particle bodies of the microcalcification which exist continuously in this way can be generated.

Figure 11A:
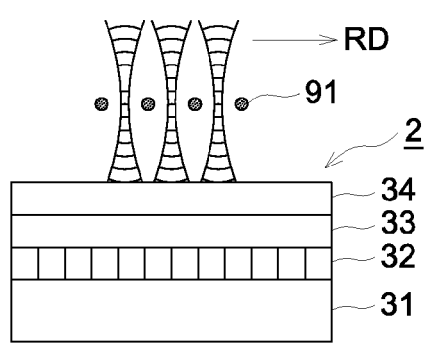
FIG. 11 is a typical diagram showing the relation between the first ultrasound wave signal transmitted from the ultrasound probe 2, and a particle body.

By the way, the first ultrasound wave signal to transmit is preferable to be an approximately plane wave in order to calculate a body of a small particle radius. FIG. 11(a) is a typical diagram showing the relation between the first ultrasound wave signal transmitted from the ultrasound probe 2, and a particle body.

Figure 11B:
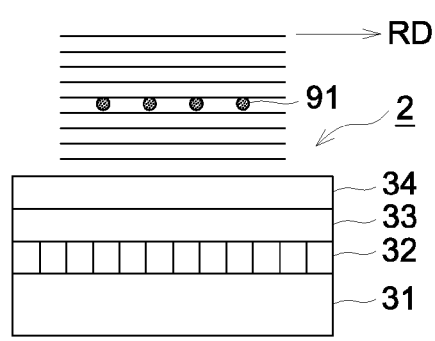

In the ultrasound diagnosis, the first ultrasound wave signal is converged in the lateral direction to form a scanning line called a sound ray and obtain a cross-sectional image of one sheet by sequentially shifting one by one, in order to calculate the minute portion in the subject to obtain the cross-sectional image. The convergence of the lateral direction is performed generally by beam forming which changes a phase in time so that the first ultrasound wave signals which the plural piezo-electric elements prepared in the ultrasound probe 2 transmit arrive simultaneously at the point to converge. If the first ultrasound wave signals are converged as mentioned above, the first ultrasound wave signals may not be irradiated to the minute particle body 91 or the irradiation intensity may become weak, as shown in FIG. 11(a). Then, as shown in FIG. 11(b), it is preferable to transmit the first ultrasound wave signal of a plane or approximately plane wave so that the first ultrasound wave signal can irradiate throughout the inside of the subject.

Specifically, a plane wave can be transmitted by adjusting the drive times of the plural piezo-electric elements to transmit the first ultrasound wave so as to make synthetic wave faces thereof to be plane.

It becomes possible to eliminate the influence of the beam intensity difference of the first ultrasound wave signal of the lateral direction RD by the difference in frequency by transmitting the first ultrasound wave signal as an approximately plane wave, as mentioned above.

Further, in this embodiment, although high order harmonics frequencies are included other than the fundamental frequency in the first ultrasound wave signal which the ultrasound probe 2 transmits, and the plural frequencies are prepared in the first ultrasound wave signal and the ultrasound image is generated from the second ultrasound wave signal corresponding to each frequency, other configuration can be used. For example, the fundamental frequency and high order harmonic frequencies may be transmitted using at least two ultrasound probes 2, and each ultrasound probe 2 may generate an ultrasound image from the second ultrasound wave signal. Further, for example, one ultrasound probe 2 may transmit individually the fundamental frequency and the high order harmonics frequencies in a series time in order, and an ultrasound image may be generated from each of the second ultrasound wave signals.

Further, in this embodiment, the cable connection or wireless connection of the ultrasound probe 2 may be made with the ultrasound diagnostic equipment main body 1.

EMBODIMENTS

Hereafter, the embodiments explain specifically the present invention although the present invention is not limited to these.

Calcium carbonate dispersing agent is employed as the particle body and a plate of the perfect reflection body is employed as a reference. The calcium carbonate dispersing agent is dispersed in water, the transmitting side of the ultrasound probe 2 is contacted to the water, the first ultrasound wave signal is transmitted, and the reflective wave is obtained. Further, the plate is immersed in water to obtain the reflective wave similarly. The first fundamental frequency $\omega 1$, the second harmonic frequency $\omega 2$, and the third harmonics frequency $\omega 3$ are contained in the ultrasound probe 2, each intensity in the reflective wave is calculated and the ratios of reflective powers are obtained as shown in Table 1. As shown in Table 1, the reflective wave is calculated for each particle radius by making the particle radii of the calcium carbonate dispersing agent into four classes. The reflective powers are normalized with the largest reflective power among the reflective powers of frequencies $\omega 1$ through $\omega 3$. There is no difference in the reflective power by frequency for the plate, and the reflective power is set as a reference value.

This result showed that the frequency dependability of reflective power became larger as the particle radius becomes smaller, and the characteristic of reflective power was acquired as shown in FIG. 8. For example, it turned out that, in the case of particles of 135-165 micrometers of particle radius, the reflective power of second harmonic wave $\omega 2$ was larger than that of the fundamental frequency $\omega 1$ and third harmonic wave $\omega 3$, and the state of b1 of FIG. 8 was shown. Further, in the case of particles of 15-25 micrometers of particle radius, it turned out that reflective power was smaller when the degree of harmonic waves was smaller, compared with the case of larger particle radius.

TABLE 1

| Particle body | Particle Diameter (μm) | Ratio of Reflective power * | | |
|---|---|---|---|---|
| | | $\omega 1$ | $\omega 2$ | $\omega 3$ |
| Calcium Carbonate Dispersing Agent | 135-165 | 0.85 | 1 | 0.89 |
| | 70-90 | 0.8 | 0.96 | 1 |
| | 30-50 | 0.43 | 1 | 0.95 |
| | 15-25 | 0.05 | 0.34 | 1 |

* Ratio of Reflective power is calculated by regarding the ratio of reflective power of the reference plate as 1.

As mentioned above, according to the embodiment, it is possible to provide an ultrasound diagnostic equipment S equipping with an ultrasound probe 2 which transmits an ultrasound wave into the subject H and receives the ultrasound wave reflected by the particle body in the subject H to acquire a received signal; displays internal body information based on the received signal; and is capable of extracting even microcalcifications which exist continuously by having a section for acquiring the received signals of which frequencies are different by each frequency, an intensity ratio calculation section which obtains the intensities of the ultrasound wave for each frequency from the obtained received signal for each ultrasound wave to calculates the intensity ratios, and a display section to display the information on the intensity ratios.

Further, according to the embodiment, it is possible to provide an ultrasound diagnostic equipment in which, in place of the display section, the intensity ratio calculation section can calculate the particle radius of the particle body based on the information on the calculated intensity ratios.

Further, according to the embodiment, it is possible to provide an ultrasound diagnostic equipment which can display the particle radius which the particle radius calculation section calculated.

Further, according to the embodiment, it is possible to provide an ultrasound diagnostic equipment which can select a particle body of an arbitrarily particle radius to be extracted and carry out imaging of the particle body, as the ultrasound diagnostic equipment can have a section which extracts and carries out imaging of the particle body which has the particle radius of the range specified automatically or arbitrarily based on the calculation result of the particle radius of a particle body.

Further, according to the embodiment, it is possible to provide an ultrasound diagnostic equipment which can extract even microcalcifications better and at the same time, calculate the radius of a particle body better, as the ultrasound probe 2 has a −20 dB fractional bandwidth which is not less than 80% and can transmit the sound wave which contains a high frequency advantageous to resolution, and also a low frequency component of a large frequency difference Further, according to the embodiment, it is possible to provide an ultrasound diagnostic equipment equipping with the ultrasound probe 2 which has the piezo-electric element which transmits an ultrasound wave and a transmitting section which drives this piezo-electric element; and can extract even microcalcifications better and, at the same time, calculates the particle radius better since the transmitting section can generate the ultrasound wave which contains many high order harmonic waves as the piezo-electric element is driven by the rectangle wave burst wave of not more than duty cycle 0.3.

Further according to the embodiment, it is possible to provide an ultrasound diagnostic equipment in which can extract even microcalcifications better and at the same time, calculates the particle radius better because the ultrasound probe 2 can eliminate the influence of the beam intensity difference of the ultrasound signal of the lateral direction RD by the difference in frequency by transmitting the ultrasound wave of a plane wave.

DESCRIPTION OF NUMERIC DESIGNATIONS

1 Main body of Ultrasound Diagnostic Equipment
2 Ultrasound Probe
3 Cable
4 Ultrasound Probe Holder
11 Operation input section
12 Transmitting section
13 Receiving section
14 Signal processing section
15 Image processing section
16 Display section
17 Control section
19 Memory section
91 Particle body
141 Data processing section
142 Memory section
fn Band pass filter
H Subject
S Ultrasound diagnostic equipment
sn Individual signal processing section

The invention claimed is:

1. An ultrasound diagnostic equipment comprising:
an ultrasound probe which transmits an ultrasound wave toward an inner part of a subject, which receives the ultrasound wave reflected by a particle body in the subject, and which outputs a received signal, wherein the particle body is a biological structure in the subject;
a signal processing circuit which is configured to: (i) measure respective intensities of a plurality of predetermined frequencies in the received signal output by the ultrasound probe, (ii) calculate, as an intensity ratio, a ratio of the respective intensities of the plurality of frequencies in the received signal with respect to each other, and (iii) calculate a particle size of the particle body based on the calculated intensity ratio; and
a memory which stores, in advance, a relation between (i) a Z function of Stenzel and (ii) a product $k \cdot a$, where a is a particle radius of the particle body, k is defined as $\omega/c$, $\omega$ is frequency of the ultrasound wave, and c is speed of the ultrasound wave, and wherein the Z function of Stenzel is directly proportional to intensity such that a ratio of Z functions of the plurality of frequencies in the received signal is the same as the intensity ratio;
wherein the signal processing circuit (i) obtains the ratio of Z functions of the plurality of frequencies in accordance with the calculated intensity ratio, (ii) compares the ratio of Z functions of the plurality of frequencies with the relation stored in the memory, (iii) identifies Z functions in the stored relation which satisfy the obtained ratio of Z functions, each of the identified Z functions corresponding to one of the plurality of frequencies in the received signal, and (iv) calculates the particle size based on at least one of the identified Z functions using the stored relation.

2. The ultrasound diagnostic equipment described in claim 1, further comprising a display which displays the particle size calculated by the signal processing circuit.

3. The ultrasound diagnostic equipment described in claim 1, wherein the signal processing circuit is further configured to extract the particle body which has the particle size in a range specified automatically or arbitrarily and to carry out imaging of the extracted particle body.

4. The ultrasound diagnostic equipment described in claim 1, wherein the ultrasound probe satisfies the following conditional expression:

$$D/C \geq 0.8,$$

where D is a bandwidth of an amplitude value which falls by −20 dB, and C is a center value of the bandwidth.

5. The ultrasound diagnostic equipment described in claim 1, further comprising a pulse generator which is configured to generate a drive electric signal to drive the ultrasound probe,
wherein the drive electric signal is a burst wave of a rectangular wave of a duty cycle of not more than 0.3.

6. The ultrasound diagnostic equipment described in claim 1, further comprising a processor which is configured to control the ultrasound probe to transmit the ultrasound wave as a plane wave.

7. The ultrasound diagnostic equipment described in claim 1, wherein: the signal processing circuit calculates the particle size by identifying at least one product k·a which corresponds to the least one of the identified Z functions corresponding to one of the plurality of frequencies, according to the stored relation, and solving for the particle size using the at least one product k·a identified according to the stored relation and the corresponding one of the plurality of frequencies $\omega$.

8. The ultrasound diagnostic equipment described in claim 7, wherein:
the memory stores a graph in which the Z function of Stenzel is plotted on a vertical axis and k·a is plotted on a horizontal axis, and the relation between the Z function of Stenzel and k·a is expressed by a curve on the graph, and
the signal processing circuit identifies the Z functions in the stored relation which satisfy the obtained ratio of Z functions of the plurality of frequencies by determining a portion of the curve in which values of the Z functions satisfy the obtained ratio of Z functions of the plurality of frequencies, and identifies the at least one product k·a which corresponds to one of the identified Z functions by determining a position on the horizontal axis of the graph which corresponds to the at least one identified Z function.

* * * * *